US007736864B2

(12) United States Patent
Schlatterer et al.

(10) Patent No.: US 7,736,864 B2
(45) Date of Patent: Jun. 15, 2010

(54) DETECTION OF INFLAMMATION

(75) Inventors: Bert Schlatterer, Berlin (DE); Regine Baeker, Potsdam (DE); Ursula Scheefers-Borchel, Gießen (DE); Hans Scheefers, Gießen (DE)

(73) Assignee: Schebo Biotech Aktiengesellschaft, Glessen (DE)

( * ) Notice: Subject to any disclaimer, the term of this patent is extended or adjusted under 35 U.S.C. 154(b) by 1118 days.

(21) Appl. No.: 10/472,860

(22) PCT Filed: Mar. 26, 2002

(86) PCT No.: PCT/EP02/03383

§ 371 (c)(1),
(2), (4) Date: Sep. 26, 2003

(87) PCT Pub. No.: WO02/077643

PCT Pub. Date: Oct. 3, 2002

(65) Prior Publication Data

US 2004/0171095 A1  Sep. 2, 2004

(30) Foreign Application Priority Data

Mar. 27, 2001  (DE)  ................................ 101 15 083

(51) Int. Cl.
*G01N 33/573* (2006.01)
*G01N 33/577* (2006.01)
*G01N 33/68* (2006.01)
(52) U.S. Cl. ........................... 435/7.4; 435/4; 435/7.94; 436/86; 436/183; 436/548
(58) Field of Classification Search ................ 435/4, 435/7.4, 7.94; 436/547, 548, 86, 173
See application file for complete search history.

(56) References Cited

U.S. PATENT DOCUMENTS 7,115,382 B1 * 10/2006 Overgaard et al. ........... 435/7.4
2008/0233597 A1 * 9/2008 Shiina et al. ................ 435/7.8

FOREIGN PATENT DOCUMENTS

CA  2 225 270 A  6/1998
WO  WO 2005/031360  *  7/2005

OTHER PUBLICATIONS

Schauf et al, "Human Physiology: Foundations & Frontiers", Times Mirror/Mosby College Publishing, 1990. p. 484.*
Atroshi F. et al., "Possible Roles of Vitamin E and Glutathione Metabolism in Bovine Mastitis" *International Journal for Vitamin and Nutrition Research*, 1987, vol. 57, No. 1, pp. 37-43, XP009008238.
Baeker R. et al., "Lipocalin-type Prostaglandin D Synthase in Milk: a New Biomarker for Bovine Mastitis" *Prostaglandins*, 2002, vol. 67, No. 1, pp. 75-88, XP004330580.
Dorta-Contreras A. J. et al., "Beta-trace Protein in the Cerebrospinal Fluid and Serum in Meningoencephalitis" *Revista De Nurologia*, Spain, 1998, vol. 26, No. 151, pp. 386-388, XP001121347.
Logdberg A. L. et al., "Immunocalins: a Lipocalin Subfamily that Modulates Immune and Inflammatory Responses" *Biochemica Et Biophysica Acta*. Protein Structure and Molecular Enzymology, 2000, vol. 1482, No. 1-2, pp. 284-297, XP004279081.
Xu S. et al., "Lipocalins as Biochemical Markers of Disease" *Biochemica Et Biophysica Acta*. Protein Structure and Molecular Enzymology, 2000, vol. 1482, No. 1-2, pp. 298-307, XP004279082.
Gerena et al., "Immunocytochemical Localization of Lipocalin-Type Prostaglandin D Synthase in the Bull Testis and Epididymis and on Ejaculated Sperm", Biology of Reproduction 62, pp. 547-556 (2000).
Sauter et al., "Biologic markers of risk in nipple aspirate fluid are associated with residual cancer and tumour size", British Journal of Cancer, (1999), 81(7), pp. 1222-1227. (Abstract).
Zia et al., "Role of Eicosanoids, histamine, and serotonin in the pathogenesis of Klebsiella pneumoniae-induced bovine mastitis", American Journal of Veterinary Research, (1987), vol. 48, No. 11, pp. 1617-1625. (Abstract).
Peter et al., "Temporal changes in metabolites of prostanoids in milk of heifers after intramammary infusion of *Escherichia coli* organisms", Prostaglandins, (1990) vol. 39, No. 4, pp. 451-457. (Abstract).

* cited by examiner

*Primary Examiner*—David A Saunders
(74) *Attorney, Agent, or Firm*—Rothwell, Figg, Ernst & Manbeck, P.C.

(57) ABSTRACT

The invention relates to a method for the detection of inflammations, in particular of inflammatory processes in the tissue of mammary glands in humans or animals, in particular in cattle and a test-kit for carrying out said method. The method is particularly suitable for the specific detection of inflammations in mammary glands, for example during testing of milk, whereby the enzyme implicated in inflammatory processes prostaglandin D synthase (PGDS) is qualitatively or quantitatively determined.

14 Claims, 5 Drawing Sheets

Fig. 4

ALQPNFEEDK FLGRWFETSGL ASNSSWFLEK

KKVLSMCKSV VAPAADGGGLN LTSTFLRKDQ

Figure 1:
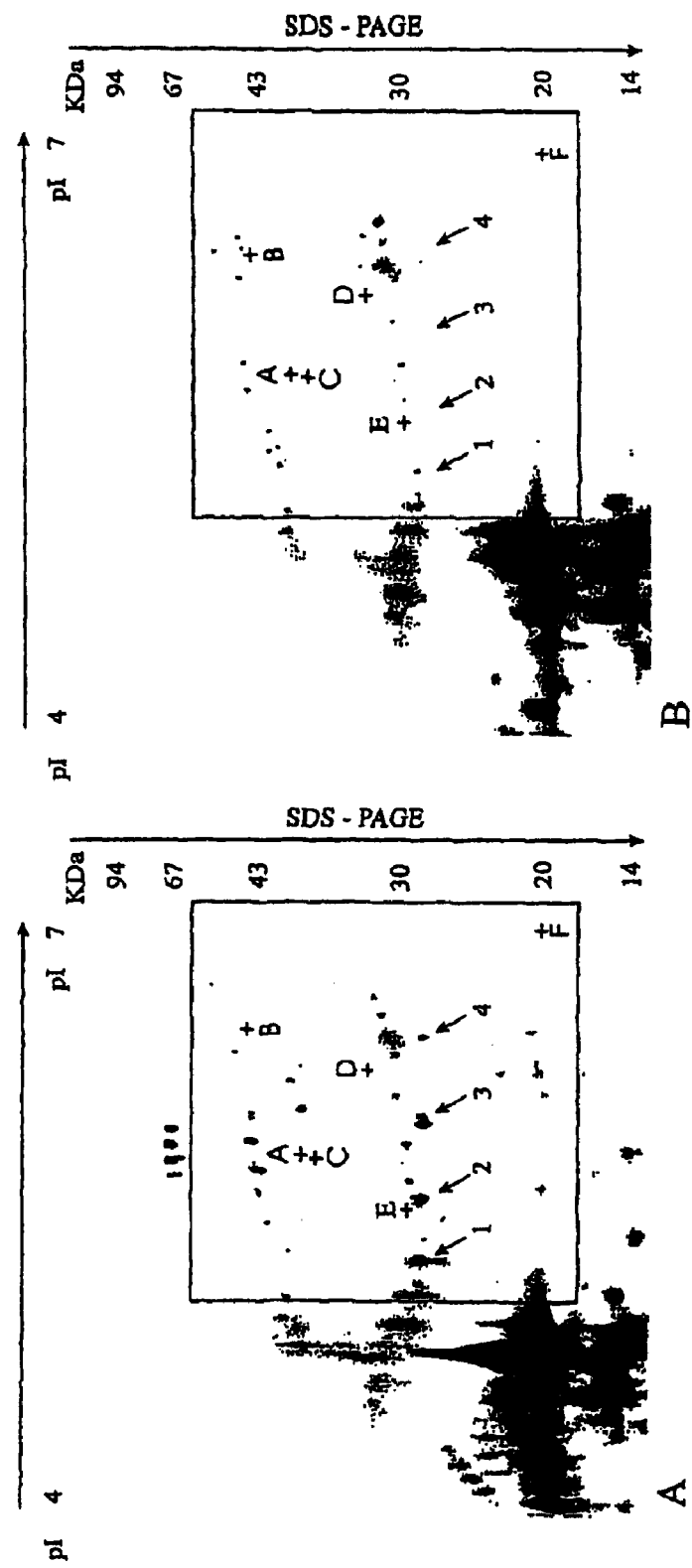

CETRTLLIRP AGPPGCYSYT SPHWSSTHEV
                *

SVAETDYETY ALLYTEGVRG PGQDFRMATL

YSRSQNPRAE VKEHFTTFAK SLGFTEEGIV

FLPKTDKCME EHP

SEQUENCE LISTING

```
<160> NUMBER OF SEQ ID NOS: 6

<210> SEQ ID NO 1
<211> LENGTH: 17
<212> TYPE: PRT
<213> ORGANISM: Unknown
<220> FEATURE:
<223> OTHER INFORMATION: prostaglandin D synthase 1 peptide

<400> SEQUENCE: 1

Leu Thr Ser Thr Phe Leu Arg Lys Asp Gln Cys Glu Thr Arg Thr Leu
1               5                   10                  15

Leu

<210> SEQ ID NO 2
<211> LENGTH: 17
<212> TYPE: PRT
<213> ORGANISM: Unknown
<220> FEATURE:
<223> OTHER INFORMATION: prostaglandin D synthase 2 peptide

<400> SEQUENCE: 2

Phe Glu Glu Asp Lys Phe Leu Gly Arg Trp Phe Thr Ser Gly Leu Ala
1               5                   10                  15

Ser

<210> SEQ ID NO 3
<211> LENGTH: 16
<212> TYPE: PRT
<213> ORGANISM: Unknown
<220> FEATURE:
<223> OTHER INFORMATION: prostaglandin D synthase 3 peptide

<400> SEQUENCE: 3

Gly Pro Gly Gln Asp Phe Arg Met Ala Thr Leu Tyr Ser Arg Ser Gln
1               5                   10                  15

<210> SEQ ID NO 4
<211> LENGTH: 163
<212> TYPE: PRT
<213> ORGANISM: Bos taurus

<400> SEQUENCE: 4

Ala Leu Gln Pro Asn Phe Glu Glu Asp Lys Phe Leu Gly Arg Trp Phe
1               5                   10                  15

Thr Ser Gly Leu Ala Ser Asn Ser Ser Trp Phe Leu Glu Lys Lys Lys
            20                  25                  30

Val Leu Ser Met Cys Lys Ser Val Val Ala Pro Ala Ala Asp Gly Gly
        35                  40                  45

Leu Asn Leu Thr Ser Thr Phe Leu Arg Lys Asp Gln Cys Glu Thr Arg
    50                  55                  60
```

```
Thr Leu Leu Leu Arg Pro Ala Gly Pro Pro Gly Cys Tyr Ser Tyr Thr
 65                  70                  75                  80

Ser Pro His Trp Ser Ser Thr His Glu Val Ser Val Ala Glu Thr Asp
                 85                  90                  95

Tyr Glu Thr Tyr Ala Leu Leu Tyr Thr Glu Gly Val Arg Gly Pro Gly
            100                 105                 110

Gln Asp Phe Arg Met Ala Thr Leu Tyr Ser Arg Ser Gln Asn Pro Arg
            115                 120                 125

Ala Glu Val Lys Glu His Phe Thr Thr Phe Ala Lys Ser Leu Gly Phe
        130                 135                 140

Thr Glu Glu Gly Ile Val Phe Leu Pro Lys Thr Asp Lys Cys Met Glu
145                 150                 155                 160

Glu His Pro

<210> SEQ ID NO 5
<211> LENGTH: 11
<212> TYPE: PRT
<213> ORGANISM: Bos taurus

<400> SEQUENCE: 5

Leu Leu Arg Pro Ala Gly Pro Pro Gly Cys Tyr
1               5                   10

<210> SEQ ID NO 6
<211> LENGTH: 10
<212> TYPE: PRT
<213> ORGANISM: Bos taurus

<400> SEQUENCE: 6

Leu Arg Pro Ala Gly Pro Pro Gly Cys Tyr
1               5                   10
```

DETECTION OF INFLAMMATION

CROSS REFERENCE TO RELATED APPLICATION

This application is a 35 USC § 371 National Phase Entry Application from PCT/EP02/03383, filed Mar. 26, 2002, and designating the U.S.

DESCRIPTION

The present invention relates to a method for detection of inflammation processes. The present invention relates in particular to a method for detection of inflammation processes in tissue in the mammary glands of humans or animals, in particular cattle, and to a test kit for carrying out the method according to the invention. The method is particularly suitable for specific detection of inflammation in mammary glands, for example by examining milk, with the enzyme Prostaglandin D Synthase (PGDS) which is involved in the occurrence of inflammation being determined qualitatively or quantitatively.

Inflammation in cattle mammary glands is of major financial importance because of the fact that it arises frequently in about 30-40% of all milk cows. On the one hand, inflammation such as this reduces the amount of milk produced and the quality of the milk for marketing. On the other hand, excessively late identification and the massive antibiotic treatment that is then required result in waiting times in which the milk cannot be marketed. Assuming that 10% of the milk yield from 15% of the milk cows in the Federal Republic of Germany is lost, this is equivalent to an average production of 6500 kg of milk, and with a price per kilogram of DM 0.45, this can be calculated to result in a financial loss of at least about DM 210 million per annum.

All diagnostic methods used so far for detection of mammary gland inflammation are non-specific and do not allow direct assessment of the inflammation processes in the mammary gland. These known methods include, for example, measurement of the electrical conductivity of the milk, determination of the cell counts or detection of enzymes which indicate that tissue damage has already occurred, such as lactatdehydrogenase. However, enzymes such as these cannot be detected until relatively late.

Currently available fast tests for on sight use are indirect tests and are based on qualitative and/or semi-quantitative detection of deoxyribonucleic acid which are released from cells contained in the milk and are assessed visually. An increased number of cells, which results in an increase in the quantity of deoxyribonucleic acid, is in this case regarded as an indicator of inflammation in the mammary glands. While the test gives an indication of the number of cells, an increased number of cells is, however, not caused directly by inflammation processes, as can be seen, for example, from the high positive result which can be observed at the start and at the end of lactation.

Since inflammation of the mammary glands is caused virtually exclusively by bacterial infections, bacteriological diagnosis should be regarded as a major factor. However, in practice, it has been found that there is rarely any correlation between the stated non-specific changes in the milk and bacteriology. Thus, until now, diagnosis in particular of subclinical inflammation has been highly uncertain. Examples of functional protein indicators for subclinical mastitis are, for example, LDH, NAGase (Zank W., Schlatterer B. Assessment of subacute mammary inflammation by soluble biomarkers in comparison to somatic cell counts in quarter milk samples from dairy cows. J Vet Med A 1998; 45:45-51), plasminogen and plasmin (Urech E., Puhan Z., Schällibaum M. Changes in milk protein fraction as affected by subclinical mastitis. J Dairy Sci 1999; 82:945-951) as well as the marker C5a (Rainard P., Poutrel B. Generation of complement fragment C5a in milk is variable among cows. J Dairy Sci 1999; 82:2402-2411).

Inflammation is generally triggered by inflammation mediators after initiation by bacterial metabolism products. Initial processes are in this case based on a locally increased phospholipid metabolism, which leads to prostaglandins and to metabolism products similar to prostaglandin. Although these can be detected in the milk secretion from an inflamed mammary gland, no substance patterns which an be assessed uniquely have, however, yet been detected or identified, and this is related inter alia to the complexity of and the effort for analysis (F. Atroshi et al. Inflammation-related changes in cyclic AMP and cyclic GMP in bovine mastitis. Vet Res Commun 1989; 13:427-33; O. O'Sullivan et al. Analysis of prostaglandin D2 metabolites in urine: comparison between enzyme immunoassay and negative ion chemical ionisation gas chromatography-mass spectrometry. Prostaglandins Other Lipid Mediat 1999; 57:149-165).

One object of the invention was therefore to provide a method and, in particular, a specific inflammation indicator for detection of mammary gland inflammation. It would also be desirable to be able to detect other inflammation processes with the aid of an inflammation indicator. A further object of the invention was therefore to provide a method for detection of inflammation.

This object is achieved by a method for detection of inflammation which is characterized in that the enzyme prostaglandin D synthase (PGDS) or parts of it is or are determined qualitatively and/or quantitatively. The determination is preferably made in bodily fluids. It has been found that the prostaglandin D synthase (PGDS) rises during inflammation processes in the body and in the tissue of humans and animals. In the case of inflammation, for example in the case of rheumatoid arthritis or encephalitis, increased amounts of PGDS can be found in bodily fluids, for example in the plasma, in the synovial fluid, in the cerebrospinal fluid, in the urine or in the ejaculate. Prostaglandin D synthase (PGDS) is thus suitable for use as an inflammation indicator for inflammation processes, since the amount of the enzyme rises when inflammation is present. The determination can also be made in the stool, and is then used to detect inflammation in the gastrointestinal tract, in particular in the stomach, pancreas or intestines.

The invention relates in particular to a method for detection of mammary gland inflammation, which is characterized in that the enzyme prostaglandin D synthase (PGDS) or parts of it is or are determined qualitatively and/or quantitatively.

It has been found that the prostaglandin D synthase (PGDS) is precipitated to an increased extent in the case of mammary gland inflammation, so that this enzyme is suitable for use as an inflammation indicator for specific qualitative and/or quantitative detection of mammary gland inflammation.

Thus, according to the invention, an indicator with high specificity and which is coupled directly to the inflammation processes is provided, whose detection and quantification also allow early diagnosis of inflammation, in particular inflammation of the mammary glands. The indicator enzyme prostaglandin D synthase (access number 002853) occurs in a number of isoforms, which can be detected individually or together.

The indicator substance PGDS for detection of mammary gland inflammation was found by comparison of the whey protein pattern of milk from animals affected by mammary gland inflammation with that from unaffected, healthy animals. This protein pattern can be obtained, for example, by two-dimensional gel electrophoresis (2D-PAGE), with four additional spots with a molecular weight of about 26 kDa and a pH range from 5.0 to 6.4 occurring in milk samples from animals with mammary gland inflammation. The substances removed from the gel showed a very similar chromatographic and mass-spectrometric pattern of chemotryptic peptides. A databank search revealed the four substances as isoforms of cattle prostaglandin D synthase (PGDS) and, in one of the isoforms, a cystein residue was oxidized to form a sulfonic acid.

Despite the highly complex nature of the defensive and inflammation mechanisms in mammary glands against the invasion of various infectious agents, it was thus possible to produce a marker which reliably allows qualitative and/or quantitative detection of mammary gland inflammation. On the basis of the large quantity of caseins in the milk, prefractionation of cattle milk proteins was carried out with respect to whey components, as a result of which it was possible to achieve a polypeptide resolution which allowed the identification of the PGDS marker enzyme according to the invention.

Surprisingly, this marker molecule could be detected not only in the blood or within the cells in the event of mammary gland inflammation, but also occurs to an increased extent in the milk in the case of mammary gland inflammation, so that easy and simple detection of mammary gland inflammation is possible. Furthermore, the enzyme could be detected to an increased extent in bodily fluids when inflammation was present, for example to an increased extent in the cerebrospinal fluid in the case of encephalitis, and in the synovial fluid in the case of rheumatoid arthritis.

Prostaglandin D synthase, which is similar to lipocalin and is also referred to as prostaglandin-H2-D-isomerase (EC5.3.99.2), is a membrane-bound enzyme (Giacomelli S., Leone M. G., Grima J. Silvestrini B., Cheng C. Y. Astrocytes synthesize and secrete prostaglandin D synthase in vitro. Biochim Biophys Acta 1996; 1310:269-276).

In principle, the method according to the invention can be used for detection of inflammation in humans or animals.

While the method according to the invention can preferably be used for detection of mammary gland inflammation in humans or animals, it is particularly preferably used for detection of mammary gland inflammation in cattle. The enzyme prostaglandin D synthase or parts of it are preferably determined, particularly parts with a length of at least 15 amino acids, and more preferably of at least 30 amino acids, and even more preferably of at least 50 amino acids, in a bodily fluid sample or preferably in a milk sample. Human prostaglandin D synthase is used in particular for detection in humans, and bovine prostaglandin D synthase is used in particular for detection in cattle. The determination of the marker in a milk sample allows quick and simple assessment on sight as to whether or not inflammation is present, and as to the severity of any inflammation.

The determination is particularly preferably made using at least one antibody to prostaglandin D synthase. Antibodies which can be used according to the invention may be produced using methods known from the prior art. Those skilled in the art will be highly familiar with methods for producing monoclonal and polyclonal antibodies. The antigen, that is to say in the present case the enzyme prostaglandin D synthase or parts of it, is or are used by way of example to produce monoclonal antibodies, usually purified in order to produce antibodies. In principle, the method which was first described by Köhler and Millstein can be used for this purpose, and those skilled in the art will also be familiar with modified forms and further developments of these methods. The selectivity of the antibodies obtained can be confirmed by selection.

On the basis of prostaglandin D synthase or parts of it, it is also possible to produce polyclonal antibodies using known methods. Polyclonal antibodies such as these are preferably used, in particular polyclonal antibodies which identify all isoforms of prostaglandin. D synthase.

The antibody is particularly preferably produced using the peptides PGDS1 (Ac-LTSTFLRKDQCETRTLL-NH2) [SEQ ID NO:1], PGDS2 (Ac-FEEDKFLGRWFTSGLAS-NH2) [SEQ ID NO:2], or PGDS3 (Ac-GPGQDFR-MATLYSRSQ-NH2) [SEQ ID NO 3].

The determination is preferably made by means of an immunoassay, in particular by means of a quantitative sandwich ELISA. In one preferred embodiment of this test, a sample, for example a milk sample to be examined, is brought into contact with at least two different receptors, the first receptor R1 of which is in an immobilized form in a solid phase and can be bonded with PGDS, while the second receptor R2 is in the liquid phase, and can likewise be bonded with PGDS and carries a marker or allows bonding to a molecule which can be detected, separates the solid phase from the liquid phase, and determines the marking or the detectable molecule in the solid phase. The amount of PGDS in the sample can be quantified by quantifying the determined amount of the marking or of the detectable molecule.

In a further preferred embodiment, the method according to the invention is carried out as a Western Blot.

When carrying out an immunoassay, it is possible to specifically determine the content of PGDS in a sample, for example in a milk sample, which can be regarded as a marker for mammary gland inflammation. In addition to the quantitative determination, a qualitative determination is also possible in order, for example, to obtain a rapid result in advance. A cut-off value is preferably defined, in order to distinguish between negative and positive results.

In one preferred embodiment, at first an antibody which specifically binds with the enzyme PGDS is immobilized in a solid phase by means of known methods. The sample to be investigated, in particular a milk sample is, after being skimmed, brought into contact with the fixed antibody in some suitable buffer solution, and is bonded via this to the solid phase. After washing the immobilized antibody enzyme complex obtained in this way, a further, secondary antibody is then added, which is coupled to a marker, which binds to a different epitope in the PGDS, and determines the amount of marker that remains in the system. The amount of the bound marker is directly proportional to the amount of PGDS in the sample. The method according to the invention is preferably carried out in parallel with reference material with different concentrations of PGDS in bodily fluid samples, in particular in milk samples, in order to provide a high level of analysis confidence and accuracy.

The method according to the invention makes it possible to detect and to quantify both inflammation that is about to start and already existing inflammation, particularly mammary gland inflammation. Furthermore, the method can be carried out specifically and easily. The method according to the invention is furthermore suitable not only for being carried out in a laboratory, for example as a quantitative test method, but may also be in the form of a quick-test variant, which allows the location and severity of inflammation to be assessed in situ.

In addition to carrying out the method according to the invention in the form of an immunoassay and, in particular, of an ELISA or a Western Blot, PGDS can also be detected, for example in milk, with the aid of other detection methods, with the detection being preferable in particular with the aid of mass spectroscopy, in particular MALDI-TOF (matrix-assisted laser desorption/ionization time of flight mass spectroscopy) or by means of gel electrophoresis, in particular two-dimensional gel electrophoresis. In addition, the analyte concentration can in principle also be determined by means of biosensors, such as amperometric sensors, potentiometric, piezoelectric, thermometric or photometric sensors, or else by means of semiconductor electrodes, such as field-effect transistors (FETs), chemosensitive field-effect transistors (CHEMFETs), suspended gate field-effect transistors (SG-FETs) or ion-sensitive field-effect transistors. Biosensors such as these are described, for example, by E. A. H. Hall and G. Hummel in "Biosensors", Springer-Verlag Heidelberg, Germany 1995. The detection can also be carried out by means of the Kandelaber technology from IBM, Inc. A particularly advantageous procedure with regard to sensitivity, dynamic measurement range, analysis kinetics and format flexibility can be achieved by the use of electrochemiluminescence technology. Electrochemiluminescence is a process in which light is released. The release of light is induced by applying an electrical potential to an electrode which mediates a cyclic redox reaction of a ruthenium metal ion (Bruno, G. (1997) Rec. Rp. pages 175-179; Williams R. (1996), Amer. Biotech., page 27). A similar suitable technology is the TRACE technology from the company CIS, Germany.

The present invention also relates to a test kit for detection and/or for diagnosis of inflammation, in particular of mammary gland inflammation, which contains at least one receptor which binds with prostaglandin D synthase, with the test kit being designed in particular for carrying out the method according to the invention. The test kit is intended in particular for detection in the case of cattle, but can also be provided for detection in the case of other animals or humans.

The antibody is preferably a polyclonal antibody which binds with a number of the isoforms, and preferably with all of the isoforms, of prostaglandin D synthase.

The receptor which binds with the enzyme PGDS preferably allows binding to a solid phase, so that it is possible to separate the liquid phase, containing the sample, in particular a milk sample, and the solid phase with the PGDS bound to it via a receptor. This solid phase is likewise a part of the test kit, in one preferred embodiment. The sample to be investigated is then brought into contact, in a suitable buffer solution, with the fixed or fixable receptor, in particular an antibody, and is bound to the solid phase by means of the receptor. When using milk as the sample, the cream is preferably removed before this step.

After washing the immobilized antibody PGDS complex that is obtained, a further marked secondary antibody, or a secondary antibody which can be bound to a detectable molecule, for example with biotin, is then added and preferably binds to another epitope of the PGDS. The marking can then be determined, for example with the aid of streptavidin peroxidase. The amount of bound marker is directly proportional to the amount of PGDS in the sample. The test kit expediently contains reference material of a known content and, in particular, with different concentrations of PGDS for quantitative determination and for analysis quality confidence.

In addition to the preferred form as a solid phase sandwich assay, the method according to the invention can also be carried out using other detection methods. In particular, all types of immunological detection methods which are carried out with the aid of antibodies can be used according to the invention. Thus, for example, the method according to the invention can be carried out as a sandwich, ELISA, oscillating crystal, microbalance or electrochemoluminescence test, and preferably contains the reactants required for this purpose, and possibly also apparatuses.

For simple handling, the test may be in the form of a test strip on which the required antibodies are arranged in different zones, for example, fixed either in soluble form or in solid phases. The sample or the liquid component of the sample or an extract of it can then migrate through the test strip and can produce a signal at the detection point when PGDS is present in the sample.

In a further preferred embodiment, the test is designed as a fast test in the form of a membrane diffusion test, for example as an immunochromatographic lateral flow test, or some similar test.

For the purposes of the present invention, the expressions "receptor" and "antibody", respectively, also means those parts or fragments of receptors or antibodies which still provide the necessary binding to PGDS. In this case, it is also possible to use a conjugate, for example composed of two antibodies, instead of a single antibody. In particular, for example, an antibody which can bind with PGDS can be used as the secondary receptor, with the detection being carried out using a further marked antibody, which is directed against the Fc part of the secondary antibody and carries a marking, or is once again cobbled to a detectable molecule. Such conjugate formation from two antibodies is also intended to be covered within the scope of the present invention, if the secondary antibody is defined such that it allows binding to a detectable molecule. An analogous situation applies to the binding of the first antibody to the solid phase. This binding can also take place via antibodies coupled to the solid phase and which bind the Fc part of the first antibody.

For the purposes of the present invention, it is preferable for the test kit to contain antibodies or antibody fragments which can bind in a specific manner as receptors. It is furthermore preferable for the first antibody to be coupled to a solid phase, while the second antibody is preferably a soluble, marked antibody or a soluble antibody which is bounded to an enzyme which can in turn be determined via a detection reaction. The marking may be designed such that it can be identified without any further additions of substances, for example a gold marking or a fluorescent marking, or else be designed so as to allow the addition of further reactants to produce the determination. For example, the detection can be made by marking with enzymes and the addition of the enzyme substrate.

A further object of the present invention is the use of an antibody against prostaglandin D synthase for producing means for detection of inflammation, in particular of mammary gland inflammation. According to the invention, it has been found that antibodies against prostaglandin D synthase are specific markers for inflammation, in particular for mammary gland inflammation, so that they can be used both for qualitative and for quantitative detection of such inflammation.

A further object of the present invention is a monoclonal antibody which specifically binds the enzyme prostaglandin D synthase (PGDS).

The antibodies according to the invention can be obtained with the aid of methods that are known per se. In this case, the enzyme prostaglandin D synthase (PGDS) is first of all isolated and if necessary purified. After this, an experimental animal can be immunized with the prostaglandin D synthase obtained in this way, or with fractions of it which have the corresponding epitopes, and the antibodies which are formed can be isolated. Fractions which are used for immunization may, for example, originate from protease digestion of the purified PGDS, or may comprise synthetic partial peptides of it. The production of such partial peptides is known per se to those skilled in the art. In this case, it is possible, for example, to use computer programs to choose from the overall sequence elements which contain appropriate epitopes. These sequences are then tested for their usefulness for producing specific antibodies.

The monoclonal antibodies according to the invention are preferably produced using the methods from Köhler, Millstein (Nature 256, 495-497 (1975)). In this case, by way of example, BALB/c mice are immunized with isolated PGDS, and the spleen cells from these animals are fused with a myeloma cell line, for example, PA I. The secreted antibodies are tested for their specific nature and are isolated using, for example, ELISA or RIA.

The present invention also relates to aptameres which specifically bind to PGDS. Aptameres are oligonucleotide sequences which have specific binding characteristics. The aptameres according to the invention may, for example, be produced and identified using the methods described in U.S. Pat. No. 5,270,163 or in Sumedha, Clin. Chem. 45 (1999) 1628-1650.

The invention will be explained in more detail using the following examples and the attached figures.

FIG. 1:

Comparison of whey protein patterns of inflamed (FIG. 1A) and unchanged (FIG. 1B) mammary gland quarters with SDS-2D-PAGE.

Equivalent amounts (6 mg) of lyophilized protein samples were loaded onto pH 4-7 linear IPG strips and were focused, followed by electrophoresis on an SDS gel with a constant acrylamide concentration (12% T, 2.67% C). Arrows indicate the identified protein species, which are not present in the unchanged udder quarter. The spots annotated with letters represent identified proteins which are normally found in any milk: A: IgG1; B: beef serum albumin fragment; C: beef serum albumin fragment; D: beef serum albumin fragment; E: K-Casein; F: EPI (secretory protein).

FIG. 2:

The reverse phase HPLC separation of the chymotryptic peptides, obtained by digestion of the proteins related to the spots 2 and 3 in the gel.

FIG. 3:

MALDI-TOF spectra in the negative ion mode of the chymotryptic peptides, which were obtained by digestion of the proteins in the spots 2 and 3 in the gel. The spectra are virtually identical apart from the peptides marked by arrows. In the spot 3, the peptides for 1.085 and 1.198 Da can be associated with the residues 68 to 77 and 67 to 77 in the PGD-S sequence. The masses of the corresponding peptides in the spot 2 are 9 Da less.

FIG. 4:

PGDS sequence [SEQ ID NO: 4]. The observed chymotryptic peptides are underlined. Peptides which are different in the spots 2 and 3 are shown in bold.

FIG. 5:

Western Blots of milk secretions from differently changed udder quarters.

EXAMPLES

Example 1

Materials and Methods

Seven cows were investigated, chosen on the basis of a bacteriological examination, with regard to the somatic cell count (SCC) and the activity of the lactate dehydrogenase (LDH). Initial milk samples of infected and uninfected quarters of the same udder were placed directly in 50 ml containers, which contained a combination of the two proteinase inhibitors PMSF (phenylmethylsulfonyl fluoride, 2 nM) and APMSF (2-(4-amidinophenyl)methanesulfonyl fluoridehydrochloride, 20 µm), both from Roche Diagnostics Mannheim. Non-spiked initial milk samples were used for determining the cell counts and the LDH activity.

1.1 Analysis and Production of Whey Fractions

SSC was measured using a Fossomatic 360 (Foss Electric, Hillerfod, Denmark). The LDH activity in skimmed milk was measured using a Beckman Synchron CX5 CE auto analyzer (Zank W, Schlatterer B. Assessment of subacute mammary inflammation by soluble biomarkers in comparison to somatic cell counts in quarter milk samples from dairy cows. J. Vet. Med. A 1998; 454:45-51). The results were expressed in LDH units (µmol/sec 1). The whey protein fractions were produced using the method by Molloy M P, Herbert B R, Yan J X, Williams K L, Gooley A A. (Identification of wallaby milk proteins separated by two-dimensional electrophoresis, using amino acid analysis and sequence tagging. Electrophoresis 1997; 18:1073-1078). In short, milk fat was separated by centrifuging 5000 g at 4° C. for 10 minutes. Casein was precipitated by increasing the acidity of skimmed milk to a pH of 4.6 using 4 M acetic acid, and was removed by centrifuging 5000 g at 4° C. and by filtration, initially by means of a paper filter and then by means of a polyvinylidene difluoride membrane (PVDF, 0.2 µm). The filtrate was dialyzed over night at 4° C. against double-distilled water. Undissolved material was removed by centrifuging. A protein determination was made based on Bradford M H. (A rapid and sensitive method for quantitation of microgram quantities of protein utilizing the principle of protein-dye binding. Anal Biochem 1976; 205:22-26) using a protein assay from Bio-Rad (Hercules, USA). Aliquots was lyophilized and stored at −70° C.

1.2 Two-dimensional Polyacrylamide Gel Electrophoresis (2D-PAGE)

1.2.1 First Dimension: Isoelectric Focusing 6 mg of lyophilized proteins from the whey fractions were dissolved in 350 µl of rehydration solution (8 M urea, 2% CHAPS, 0.3% dithioerythritol (DDT), 2% IPG puffer). Immobiline™ Dry Strips, pH 4-7, 18 cm, were used on Multiphor II apparatus (Amersham Pharmacia Biotech, Uppsala, Sweden). The focusing was started at 500 V. The voltage was increased in steps to 3500 V within one hour, and the focusing was continued at 2 mA and 10 W for 7.5 hours.

1.2.2 Second Dimension: SDS Polyacrylamide Gel Electrophoresis

Before the second dimension, IPG strips were first of all converted to an equilibrium form in 10 ml of 50 mM Tris-HCl, pH 8.8, 6 M urea, 30% (vol/vol) glycerin, 2% (weight/volume) SDS, a trace bromophenol blue and 65 mM dithioerythritol (DDT) for 15 minutes, and were then placed in the same buffer for a further 15 minutes, with DTT being replaced by 260 mM of iodoacetamide. The IPG strips in an equilibrium form were embedded in 0.5% agarose on the cathode side on an SDS gel with a constant acrylamide concentration (12% T, 2.67% C, 200×205×1.5 mm), using the horizontal Protean® II-apparatus (Bio-Rad, Richmond, USA). The electrophoresis conditions were 150 V, 15 mA/gel, 10 W at 12° C. over night, until the bromophenol detection dye appeared at the anode end. The gels were dyed using Coomassie blue R 350 until the required dye intensity was obtained. The color was removed from the gels by repeatedly changing a dye removal solution (25% ethanol, 8% acidic acid).

1.3 Identification and Analysis of the Gel-dissolved Protein 1.3.1 Proteolytic Digestion of the Proteins in the Gel and Extraction of the Peptides The dyed protein spots were cut out and the dye was removed over 2-6 hours in a mixture of 40% (vol/vol) acetonitrile and 60% (vol/vol) 50 mM $NH_4HCO_3$. After drying by vacuum centrifuging, they were impregnated with a chymotrypsin solution (30 ng/µl in 50 mM $NH_4HCO_3$). The digestion process was carried out over night at room temperature. The peptides were extracted by the addition of 30 µl 0.1% trifluoroacetic acid (TFA) followed by 50 µl of acetonitrile ($CH_3CN$), after 10 minutes. The residue was removed and the procedure was repeated once. The combined residues were lyophilized.

1.3.2 RP-HPLC (Reverse Phase High-pressure Liquid Chromatography) Separation of the Chymotryptic Peptides The peptides formed by enzyme digestion (chymotrypsin) were separated by means of RP-HPLC (SMART system, Pharmacia, Uppsala, Sweden) on a Pharmacia C2/C18 SC2.1/10 column using a linear (0-50% in 40 min) acetonitrile gradient in 0.1% TFA. The peptides were detected at a wavelength of 214 nanometers.

1.3.3 MALDI-TOF Mass Spectroscopy

MALDI-TOF (matrix-assisted laser desorption/ionization time of flight mass spectroscopy) mass spectra were produced on a Reflex II MALDI-TOF instrument (Bruker-Daltonik, Bremen, Germany). All the spectra were recorded in the reflector mode using α-cyano-4 hydroxycinnamic acid (15 mg/ml in 70% acetonitrile) as a matrix. For mass-spectrometric analysis, the peptide mixture was dissolved in 10 µl of a ~3/7 mixture (vol/vol) of acetonitrile and 2% aqueous TFA. Individual peptides, purified by means of RP-HPLC, were subjected to a further analysis by recording the post-source decay spectra.

1.4 Data Bank Search

The data bank search using the proteolytic peptide masses was carried out using the Peptide Search Program developed by the EMBL Protein & Peptide Group (http://www.mann.embl-heidelberg.de or http://www.peptsearch.protana.com). Peptide Search uses a non-redundant protein databank which at the moment contains more than 465,000 entries. The identification of the proteins is based on the comparison of the set of peptide masses, which were derived experimentally from the isolated proteins, with the theoretical masses, derived on an enzyme basis, of the peptides, derived on an enzyme basis, for all the protein sequences in the databank.

2. Results 2.1 Inflammation Marker

Selection criteria for subclinically inflamed mammary gland quarters were LDH activities of more than 2 µmol/sec l, somatic cell counts of more than 250,000 ml$^{-1}$ and, where determined, positive bacteriological results. Only changed quarters and unchanged quarters of the same udder were used for comparison purposes. The udder quarters of the selected cows which were examined are shown in Table 1.

TABLE 1

Individual cows with inflamed (1) and unchanged (2) mammary gland quarters

| COW | QUARTER | LDH-UNITS µmol/sec l | SCC | MICROBIOLOGY |
| --- | --- | --- | --- | --- |
| 1 | 1 | 12.23 | 9 911 000 | not determined |
|   | 2 | 1.21 | 30 000 |   |
| 2 | 1 | 19.19 | 5 784 000 | not determined |
|   | 2 | 4.22 | 203 000 |   |
| 3 | 1 | 16.50 | 5 010 000 | not determined |
|   | 2 | 1.67 | 29 000 |   |
| 4 | 1 | 2.53 | 984 000 | streptococcus spp. |
|   | 2 | 1.06 | 29 000 |   |
| 5 | 1 | 17.42 | 4 048 000 | staphylococcus spp. |
|   | 2 | 1.58 | 162 000 |   |
| 6 | 1 | 28.11 | 7 697 000 | streptococcus spp. |
|   | 2 | 2.86 | 50 000 |   |
| 7 | 1 | 5.21 | 1 436 000 | staphylococcus spp. |
|   | 2 | 0.99 | 71 000 |   |

2.2 SDS-2D-PAGE Visualization of the Whey Fractions

The clearest difference in the 2D-PAGE patterns is the appearance of four spots in the whey fractions, which were obtained from inflamed quarters, compared with those from the respective internal controls. For a molecular weight of 26 kDa, these spots are arranged over a pI range from 5.2 to 6.2, and are marked with the numbers 1-4 in FIG. 1.

2.3 Identification of the Proteins Within the Spots

Figure 2:
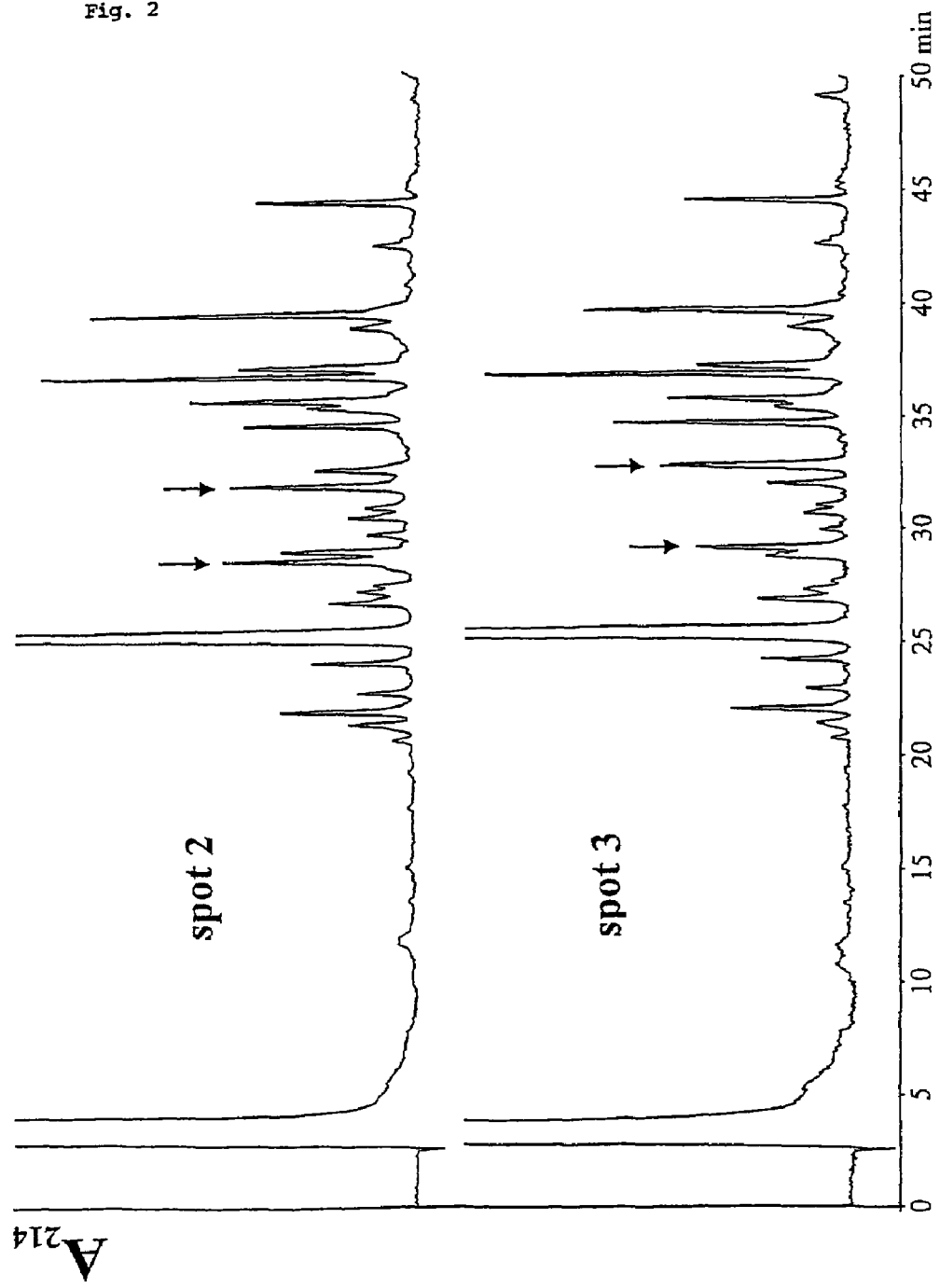
Figure 3:
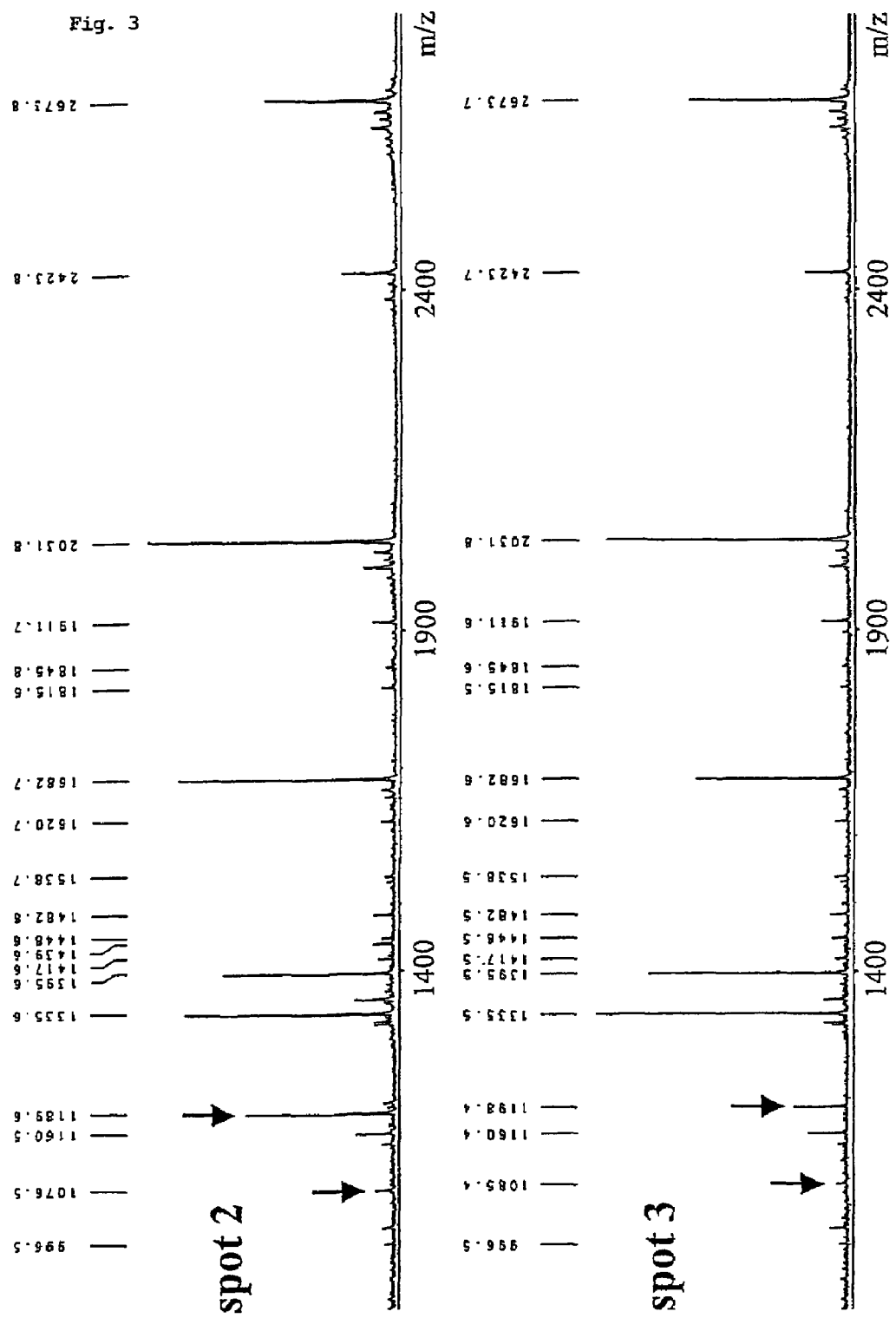
Figure 5:
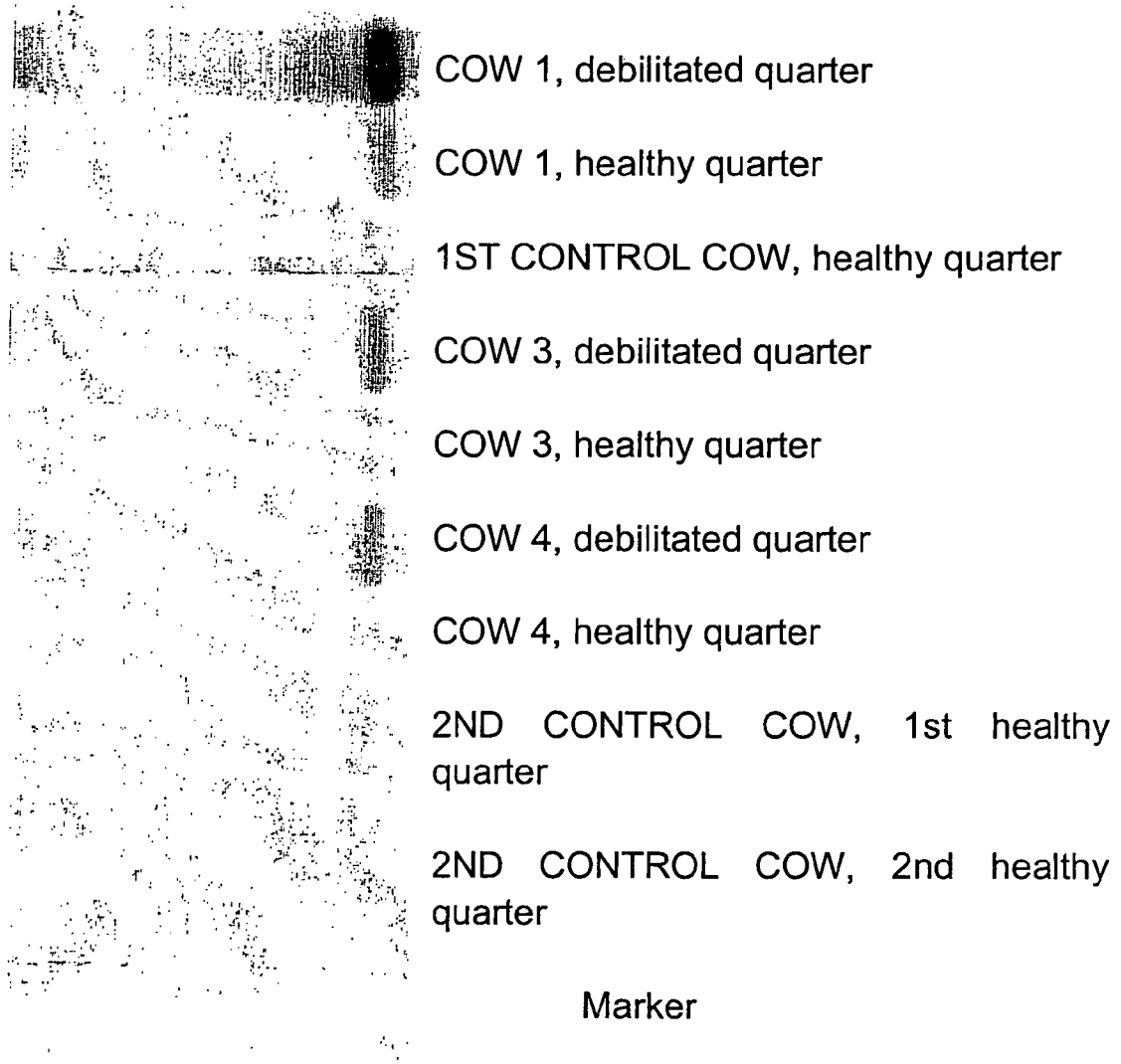

The spots 1-4 which were cut out of the 2D gels resulted in very similar chromatographic and mass-spectrometric patterns of chymotryptic peptides (FIGS. 2 and 3 show the patterns obtained for the spots 2 and 3). A databank search based on the peptide masses that were found allowed the proteins to be identified without any doubt as lipocalin-like prostaglandin D synthase (access number O02853). The mass-spectrometric data also made it possible to confirm that the ripe protein starts at residue 39 in the databank sequence.

When the peptide patterns obtained from the spots 2 and 3 are compared, two differences can be detected, as indicated by the arrows in FIG. 2 and FIG. 3. The corresponding peptides for the spot 3 can be associated with the sequence sections LLRPAGPPGCY [SEQ ID NO: 5] and LRPAGPPGCY [SEQ ID NO: 6] (see FIG. 4). The corresponding peptides for the spot 2 show a mass difference of −9 Da. Post-source decay spectra for the two peptides isolated by means of RP-HPLC made it possible to associate the modification with a cystein residue in position 76 of the ripe protein. The mass difference of −9 Da. corresponds to the difference between a cystein alkylated using an iodoacetamide and a cystein oxidized to form sulfonic acid. This also matches the observation that the isoelectric point of the modified protein is shifted toward an acidic value. The modification by iodoacetamide (spot no. 3) occurs during the gel electrophoresis conditions in the second equilibration step while, in contrast, the oxidized cystein (spot 2) occurs even before the 2D gel electrophoresis as a sulfonic acid derivative. Since the introduction of a sulfonic acid group has a major influence on the isoelectric point of a protein, the various oxidized cysteins may explain the observation of a number of gel spots with very similar molecular weights but with a different pI. The different spots may, however, also be caused by a post-translational modification, such as a heterogeneous glycosylation pattern.

Example 2

Western Blot

Western Blots were produced from milk secretions from differently changed udder quarters. The polyclonal antibodies used for the Blot were produced against prostaglandin D synthase from bovine sperm.

Pairs from the same cow were in each case used for the comparison. The debilitated mammary glands show clear coloring at the corresponding position at which the polyclonal antibody was applied. For cow 1, the "healthy" quarter was likewise on the way to becoming inflamed, which indicates that the method according to the invention makes it possible to identify mammary gland inflammation even at a very early stage. In order to ensure reliable discrimination between positive (that is to say inflamed) and negative (that is to say healthy) results, a cut-off value can be defined, and/or reference samples can also be measured at the same time.

The invention claimed is:

1. A method for detecting inflammation in a subject comprising:
   obtaining a sample from bodily fluid or milk of the subject; and
   determining prostaglandin D synthase (PGDS) or parts having a length of at least 15 amino acids in the sample, wherein determination of PGDS or parts in the sample indicates mammary gland inflammation.

2. The method as claimed in claim 1, wherein the subject is a human.

3. The method as claimed in claim 1, wherein the subject is cattle and the inflammation is mammary gland inflammation in cattle.

4. The method as claimed in claim 1, wherein the bodily fluid sample is chosen from plasma, synovial fluid, or urine.

5. The method as claimed in claim 1, wherein prostaglandin D synthase (PGDS) is determined using at least one antibody against prostaglandin D synthase (PGDS).

6. The method as claimed in claim 5, wherein the antibody is at least one antibody selected from a polyclonal against prostaglandin D synthase (PGDS).

7. The method as claimed in claim 5, wherein the antibody is obtained using as an immunogen at least one of the peptides PGDS1 (SEG ID NO:1—amino acids 51-57 of SEQ ID NO:4), PGDS2 (SEQ ID NO:2—amino acids 6-22 of SEQ ID NO:4) or PGDS3 (SEQ ID NO:3—amino acids 110-125 of SEQ ID NO:4).

8. The method as claimed in claim 1, wherein prostaglandin D synthase (PGDS) is determined using immunoassay.

9. The method as claimed in claim 8, wherein the immunoassay is a quantitative sandwich ELISA or a Western Blot.

10. The method as claimed in claim 1, wherein prostaglandin D synthase (PGDS) is determined using gel electrophoresis.

11. The method as claimed in claim 10, wherein the gel electrophoresis is two-dimensional gel electrophoresis.

12. The method as claimed in claim 1, wherein the subject is an animal.

13. The method as claimed in claim 5, wherein the antibody is at least one antibody selected from a monoclonal antibody against prostaglandin D synthase (PGDS).

14. A method for detecting inflammation in a subject comprising:
   obtaining a sample from bodily fluid of the subject; and
   determining prostaglandin D synthase (PGDS) or parts having a length of at least 15 amino acids in the sample, wherein determination of PGDS or parts in the sample indicates rheumatoid arthritis.

* * * * *